United States Patent [19]

Richardson et al.

[11] Patent Number: 5,690,653
[45] Date of Patent: *Nov. 25, 1997

[54] SUTURING APPARATUS

[76] Inventors: Philip Richardson; Margaret Pamela Richardson, both of Lluest, Cynwyl Elfed, Carmarthen Dyfed, SA33 6TL, United Kingdom

[*] Notice: The term of this patent shall not extend beyond the expiration date of Pat. No. 5,454,823.

[21] Appl. No.: 492,271

[22] Filed: Jul. 24, 1995

Related U.S. Application Data

[63] Continuation of Ser. No. 192,936, Feb. 7, 1994, Pat. No. 5,454,823, which is a continuation of Ser. No. 954,013, Sep. 30, 1992, abandoned.

[30] Foreign Application Priority Data

Sep. 30, 1991 [GB] United Kingdom ............... 9120871.0

[51] Int. Cl.⁶ .................................................. A61B 17/04
[52] U.S. Cl. ........................................................ 606/148
[58] Field of Search ................................. 606/144–148

[56] References Cited

U.S. PATENT DOCUMENTS

| | | |
|---|---|---|
| 1,037,864 | 9/1912 | Carlson et al. . |
| 1,131,163 | 3/1915 | Saunders et al. . |
| 1,293,565 | 2/1919 | Smit . |
| 1,449,087 | 3/1923 | Bugbee . |
| 1,876,792 | 9/1932 | Thompson . |
| 2,213,830 | 9/1940 | Anestasi . |
| 2,880,728 | 4/1959 | Kights . |
| 3,090,386 | 5/1963 | Curtis . |
| 3,349,772 | 10/1967 | Rugg . |
| 3,470,875 | 10/1969 | Johnson . |
| 3,807,407 | 4/1974 | Schweizer . |
| 3,842,840 | 10/1974 | Schweizer . |
| 3,901,244 | 8/1975 | Schweizer . |
| 3,946,740 | 3/1976 | Bassett . |
| 4,021,896 | 5/1977 | Stierlein . |
| 4,109,658 | 8/1978 | Hughes . |
| 4,161,951 | 7/1979 | Scanlan . |
| 4,164,225 | 8/1979 | Johnson et al. . |
| 4,236,470 | 12/1980 | Stenson . |
| 4,345,601 | 8/1982 | Fukuda . |
| 4,373,530 | 2/1983 | Kilejian . |
| 4,471,781 | 9/1984 | DiGiovanni et al. . |
| 4,491,135 | 1/1985 | Klein . |
| 4,580,567 | 4/1986 | Schweizer et al. . |

(List continued on next page.)

FOREIGN PATENT DOCUMENTS

| | | |
|---|---|---|
| 0482881 | 4/1992 | European Pat. Off. . |
| 337579 | 9/1904 | France . |
| 9109097 | 10/1991 | Germany . |
| 4124383 | 5/1992 | Germany . |
| 9203041 | 6/1992 | Germany . |
| 4124381 | 8/1992 | Germany . |
| 4127812 | 2/1993 | Germany . |
| 4139628 | 3/1993 | Germany . |
| 1103854 | 7/1984 | U.S.S.R. . |
| 1505514 | 9/1989 | U.S.S.R. . |
| 1725847 | 4/1992 | U.S.S.R. . |
| 1249853 | 10/1971 | United Kingdom . |
| 9301750 | 2/1993 | WIPO . |

OTHER PUBLICATIONS

Aesculap Catalog, p. 401 (Date: 1905).

*Primary Examiner*—Michael Buiz
*Assistant Examiner*—Tinh T. D. Pham

[57] ABSTRACT

Surgical suturing apparatus comprises upper and lower jaw elements selectively movable relative to one another between open and closed position. Each jaw element is provided with a respective recess arranged to receive a portion of an elongate incision member or length of surgical thread and securing means is provided arranged to selectively secure the surgical incision member or length of surgical thread in a respective recess. The jaw elements are typically provided at an end of an elongate positioning and operating arm making the device particularly useful for use in laparoscopic surgery.

25 Claims, 6 Drawing Sheets

U.S. PATENT DOCUMENTS

| | | |
|---|---|---|
| 4,621,640 | 11/1986 | Mulhollan et al. . |
| 4,635,638 | 1/1987 | Weintraub et al. . |
| 4,890,615 | 1/1990 | Caspari et al. . |
| 4,923,461 | 5/1990 | Caspari et al. . |
| 4,935,027 | 6/1990 | Yoon . |
| 4,957,498 | 9/1990 | Caspari et al. . |
| 5,059,201 | 10/1991 | Asnis . |
| 5,100,421 | 3/1992 | Christsudias . |
| 5,171,257 | 12/1992 | Forzei . |
| 5,181,919 | 1/1993 | Beraman et al. . |
| 5,207,693 | 5/1993 | Phillips . |
| 5,217,471 | 6/1993 | Burkhart . |
| 5,242,458 | 9/1993 | Bindel et al. . |
| 5,254,126 | 10/1993 | Filipi et al. . |
| 5,261,917 | 11/1993 | Hasson et al. . |

SUTURING APPARATUS

This is a continuation, of U.S. application Ser. No. 08/192,936 filed Feb. 7, 1994 now U.S. Pat. No. 5,454,823, which is a continuation of U.S. application Ser. No. 07/954,013, filed Sep. 30, 1992 now abandoned.

FIELD OF THE INVENTION

The present invention is concerned with surgical apparatus for sewing and suturing.

BACKGROUND OF THE INVENTION

A common surgical procedure for attaching materials together is sewing. In the case of surgical procedures a wound is closed by the manual application of a suture thread installed by means of a needle attached to the suture thread. Needle passage through tough tissue is often necessary and as such the needle must be rigid and sharply pointed. In the case of surgical suturing the needle is sometimes positioned and manouvered by the use of instruments to avoid direct handling of the needle. Even so the medical operative often experiences difficulty forcing the needle through tissue. This has limited the application of suturing to tissues which are readily accessible to the surgeon. The forceful use of a sharp needle sometimes results in needle stick injury to medical personnel. Needle stick injury has been cited as a probable cause for transmission of disease from medical personnel to patient and vice-versa. In particular, suturing or sewing of internal body tissue is extremely difficult in laparoscopic surgery, where suturing instruments must necessarily be operated remote from the tissue being sutured since the instrument must pass along a trocar into the body of the patient.

SUMMARY OF THE INVENTION

According to the invention, there is provided surgical apparatus comprising upper and lower jaw elements selectively movable between a first position in which portions of the respective jaw elements are positioned relatively close together and a second position in which said portions of said respective jaw elements are positioned relatively further apart, each of said jaw elements being provided with a respective recess or channel arranged to receive a portion of an elongate surgical incision member or length of surgical thread, and respective selectively actuable securing means arranged to secure said surgical incision member or length of surgical thread in a respective said recess relative to said respective jaw elements.

It is preferred that the upper and lower jaw elements are pivotally movable relative to one another, with advantageously one of the upper or lower jaw elements being pivotally connected to the remaining jaw element or a member to which the remaining jaw element is connected.

Typically, selective relative motion is preferably effected by means of exertion of force by an actuation member on one of the respective jaw elements. The force actuation member may exert alternately compressive, and tensile forces on the respective jaw element in moving said jaw elements between said first and second positions, and may be actuated by means of mechanical linkage, hydraulic actuation, pneumatic actuation or electrical means (e.g. actuation by means of solenoid).

Typically, where pivotal relative motion of the jaw elements is effected by exertion of a tensile/compressive force on one of the jaw elements, the respective jaw element is provided with an extended lever portion extending away from the pivotal connection to which the tensile force actuation member is connected.

It is preferred that the recesses (or channels) provided in respective upper and lower jaw elements are configured and shaped such that the surgical incision member or portion of stiffened surgical thread may be selectively removed from either recess (or channel) whilst a respective portion of the incision member or thread remains secured in the other respective recess (or channel).

Advantageously, the incision member or portion of stiffened surgical thread is arcuately curved in its longitudinal direction. Typically the respective recesses (or channels) in upper and lower jaw elements are correspondingly arcuately curved along their length.

It is preferred that the respective recesses (or channels) in the upper and lower jaw elements are arranged such that respective spaced portions of the elongate incision member or portion of surgical thread may be received in both recesses (or channels) simultaneously. Advantageously one of the recesses (or channels) provided in a respective jaw element, preferably the lower jaw element, is in the form of a hole or bore extending through the respective jaw. It is preferred that one of the recesses (or channels) provided in a respective jaw element is in the form of a slot extending substantially wholly through the respective jaw element. Advantageously the slot tapers from a mouth portion to an apex portion. The presence of the slot in one of the jaw elements enables the surgical thread to be removed from the respective jaw members whilst the incision member is still received in the other jaw element, when the jaw elements are orientated in the second position.

The securing means preferably includes a respective securing element selectively actuable to engage respective portions of the incision member or surgical thread or complementary engagement formations provided thereon such that respective portions of the incision member or thread are secured relative to the upper or lower jaw element. Advantageously the securing elements are actuable so as to individually and separately selectively engage the respective portions of the incision member or surgical thread. Actuation of the securing elements may be by means of mechanical linkage, hydraulic actuation, pneumatic actuation or by electrical actuation (e.g. actuation by means of a solenoid).

Typically, upper and lower jaw elements are provided at the distal end of an elongate positioning arm, the proximal end of which arm is preferably provided with control means for controlling the actuation of the jaw element motion and of the securing means.

Advantageously, the elongate positioning arm is substantially hollow such that mechanical linkages or hydraulic/pneumatic linkages may extend internally along the length of the arm from the control means at the proximal end of the arm to the jaw elements and securing means provided at the distal end of the arm.

Typically, the external dimensions of the elongate arm are such that the arm may be inserted and received in an elongate surgical trocar.

The invention will now be further described in a specific embodiment, suitable for use in laparoscopic surgery, by way of example only.

DETAILED DESCRIPTION OF THE PREFERRED EMBODIMENT

Figure 1:
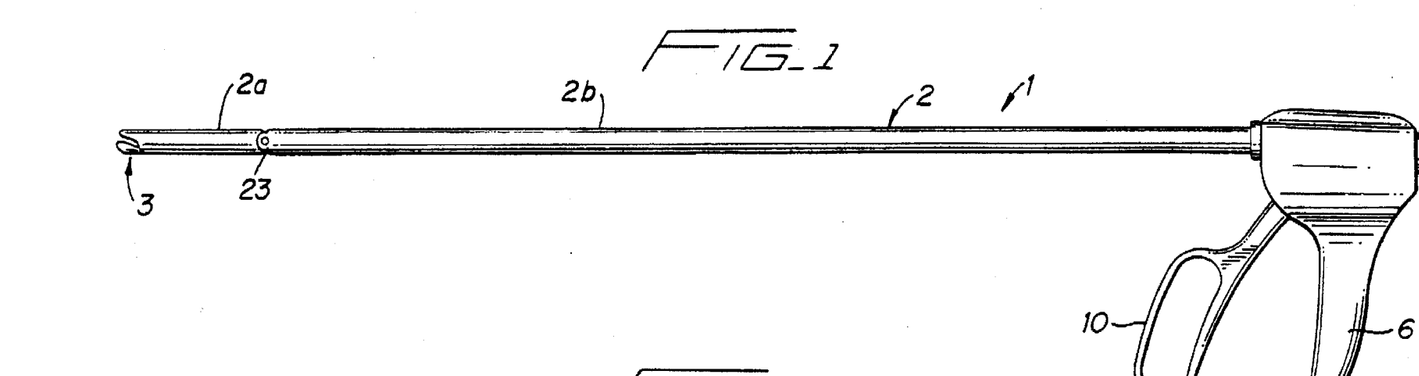
FIG. 1 is a side elevation of surgical apparatus according to the invention.

Referring to the drawings, and initially to FIG. 1 in particular, the surgical apparatus generally designated 1 is intended for use as a suturing apparatus. The apparatus 1 comprises an elongate hollow arm 2 divided into two arm portions 2a and 2b connected together at a pivotal connection joint 23 such that arm positions 2a and 2b may pivot relative to one another. At one end of the arm 2 is a suturing arrangement 3 comprising an upper jaw extension 4 integral with the arm portion 2a and a pivotal lower jaw 5 pivotally connected to the arm portion 2a. At the opposite end of the arm 2 is a handle 6 to be gripped by the user, and actuation trigger 10 for controlling the operation of the suturing arrangement 3 as described below.

Figure 2:
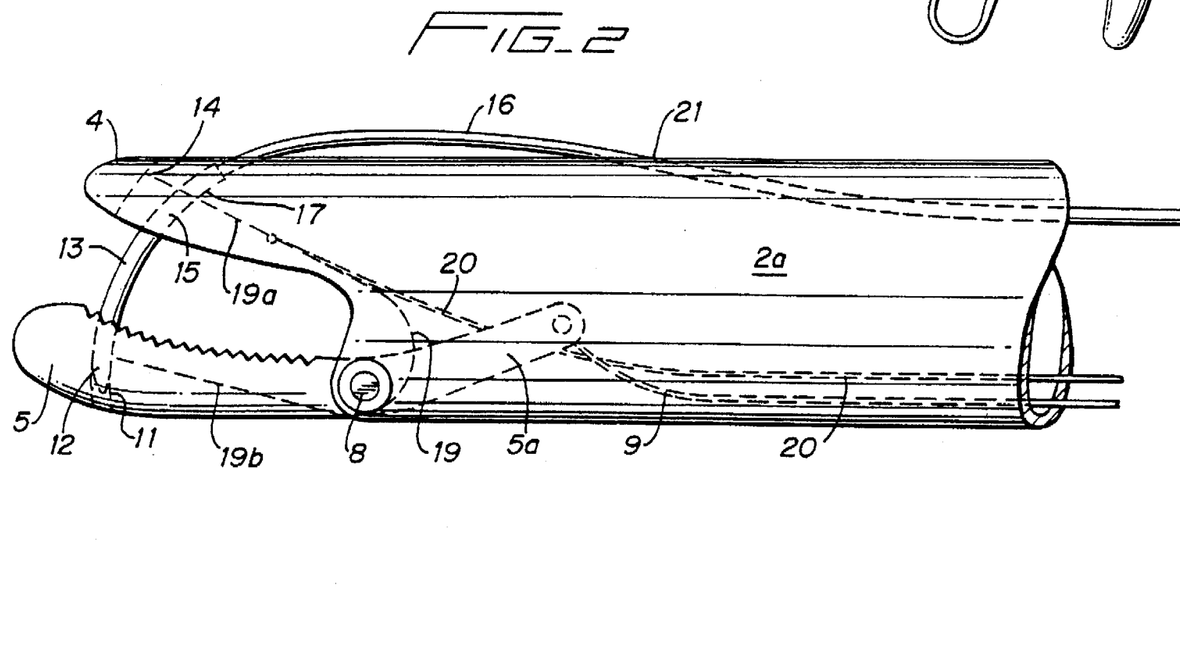
FIG. 2 is a detailed view of a part of the apparatus shown in FIG. 1.

Referring now to FIG. 2, the suturing arrangement 3 is shown in detail with pivotal connection 8 between the lower jaw 5 and arm portion 2a clearly shown. A lever extension portion 5a of the lower jaw 5 extends away from the pivot point 5 and is connected at its end to one end of a stiff actuation cable 9. The actuation cable 9 extends internally along the length of the arm 2 and is connected at its other end to the actuation trigger 10. Movement of the actuation cable 9 along the length of the arm 2 towards or away from the suturing arrangement 3 by means of manipulation of the actuation trigger 10 will cause the lower jaw 5 to pivot about pivot point 8 and the jaws to move relative to one another towards an open position with jaws 4,5 splayed apart (as in FIG. 3), or a closed position with jaws 4,5 relatively close together (as in FIG. 1), respectively.

Figure 5:
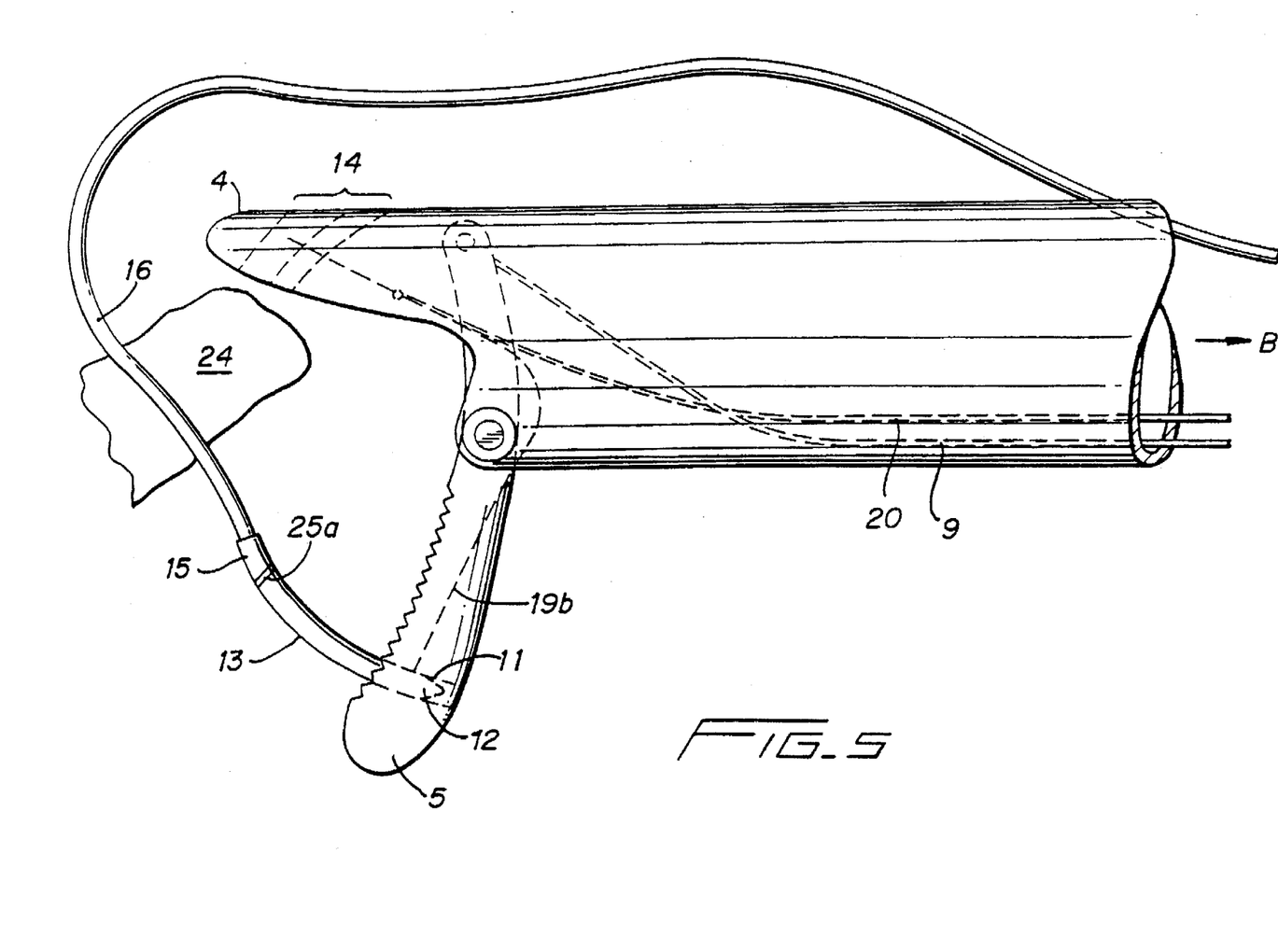
Figure 7:
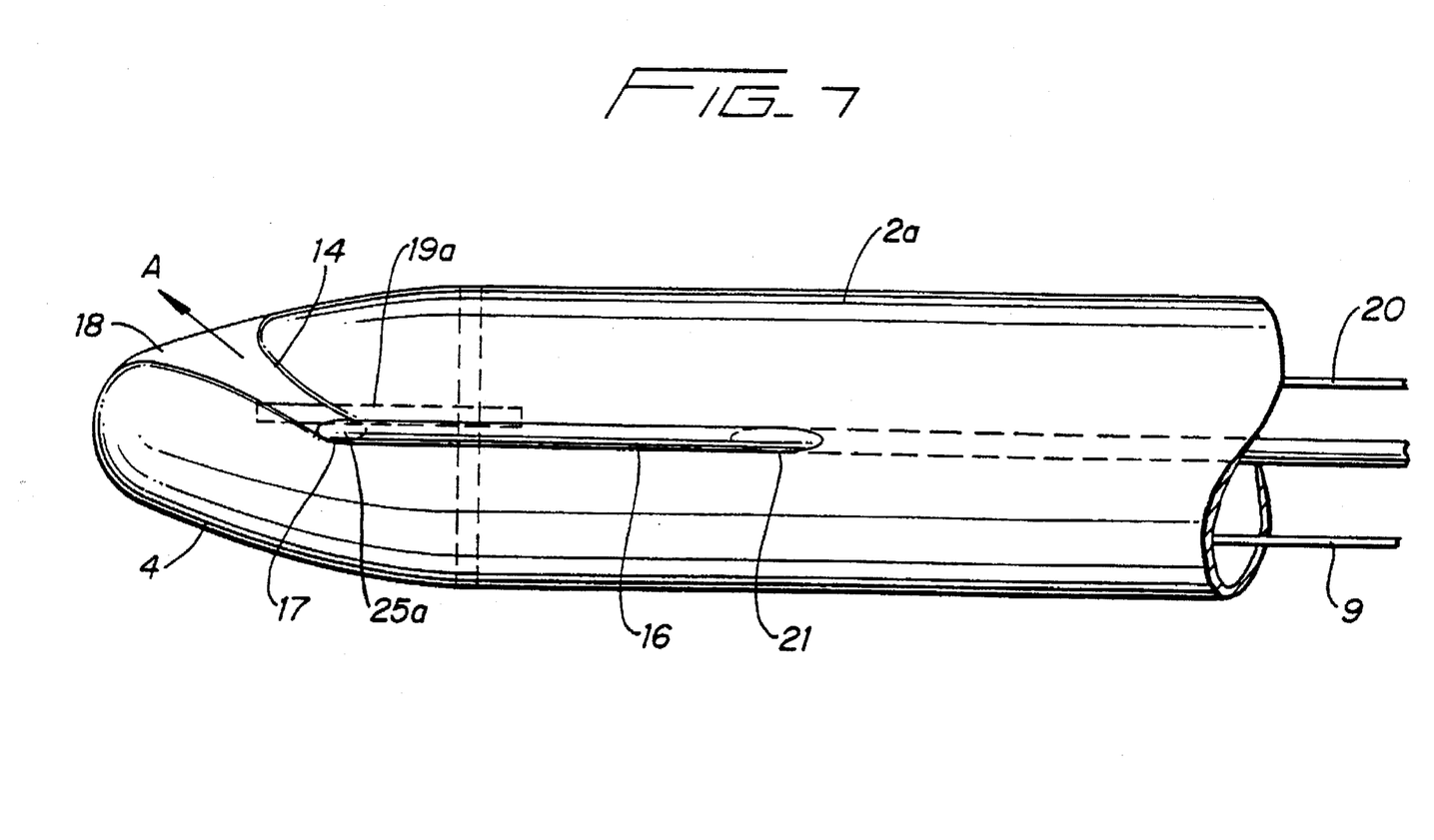
FIG. 7 is a detailed plan view of the part of the apparatus of FIG. 1 shown in FIGS. 2 to 5.

The lower jaw 5 is provided with a bore 11 of circular cross-section extending therethrough from the upper surface of the jaw. In use, the incisor end 12 of an adapted surgical needle 13 may be snugly received in the bore 11. The upper jaw 4 is provided with a generally V shaped slot 14 extending right the way through the upper jaw 4 (as is best shown in FIG. 7). in use, the trailing end 15 of the adapted surgical needle (which is attached to suturing thread 16) may be received snugly in the apex 17 of the "V" shaped slot 14 with the incisor end 12 of the needle 13 extending downwardly from the upper jaw 4 and the suture thread 16 extending upwardly from the upper jaw 4. In the open position as shown in FIG. 5, thread 16 may be removed from the slot 14 in the upper jaw 4 by moving the thread to relatively towards the mouth 18 of the "V" shaped slot 14 in the direction shown by arrow A in FIG. 7.

A flexible resilient "U" shaped metal securing member 19 having securing arms 19a and 19b which are constrained to move along defined guide channels (not shown) in the upper and lower jaws 4,5 is provided. The upper arm 19a of the securing member 19 is connected to one end of a second stiff actuation cable 20 which also extends along the length of the arm 2 to the actuation trigger 10. Further movement of the actuation trigger 10 once it has been moved to either open or close the jaws 4,5 causes the respective securing arms 19a and 19b to slide along their defined guide channels in respective jaws 4,5 and intersect the "V" shaped slot 14 or bore 11 respectively. Where a respective portion of the adapted needle 13 is present in the bore 11 or slot 14, the respective arm 19b, 19a will engage with that a respective notch portion 25a, 25b of the needle 13 and secure it in the slot or hole.

As shown in the drawings, due to the securing action of the securing member 19, when securing arm 19a intersects slot 14 and engages notch 25a in needle 13, the arm 19b is withdrawn from bore 11, and vice versa. Thus at all times, the needle is positively secured in either jaw 4 or jaw 5.

It should be noted at this point that whilst the device is described for use with an adapted needle, a suture thread with a suitably stiffened end portion would serve adequately, negating the necessity for a needle.

The thread 16 extends upwardly out of the slot 14 in the upper jaw 4, and then re-enters the hollow arm 2 through an aperture 21. The thread then extends internally along the length of the arm 2 where it is connected at the handle end of the device to a spool (not shown).

In use, the apparatus is loaded with needle 13 attached to thread 16 by inserting the needle through slot 14 and with the tip 12 extending into bore 11. Upper securing arm 19a is then actuated forwardly by means of manipulation of the trigger 10 to intersect the slot 14 and engage in notch 25a in the upper portion 15 of the needle 13 and securely hold the needle 13 in the slot 14 relative to the upper jaw 4. At this stage the condition of the apparatus is as shown in FIG. 2 with the lower securing arm 19b retracted from the bore 11.

Figure 3:
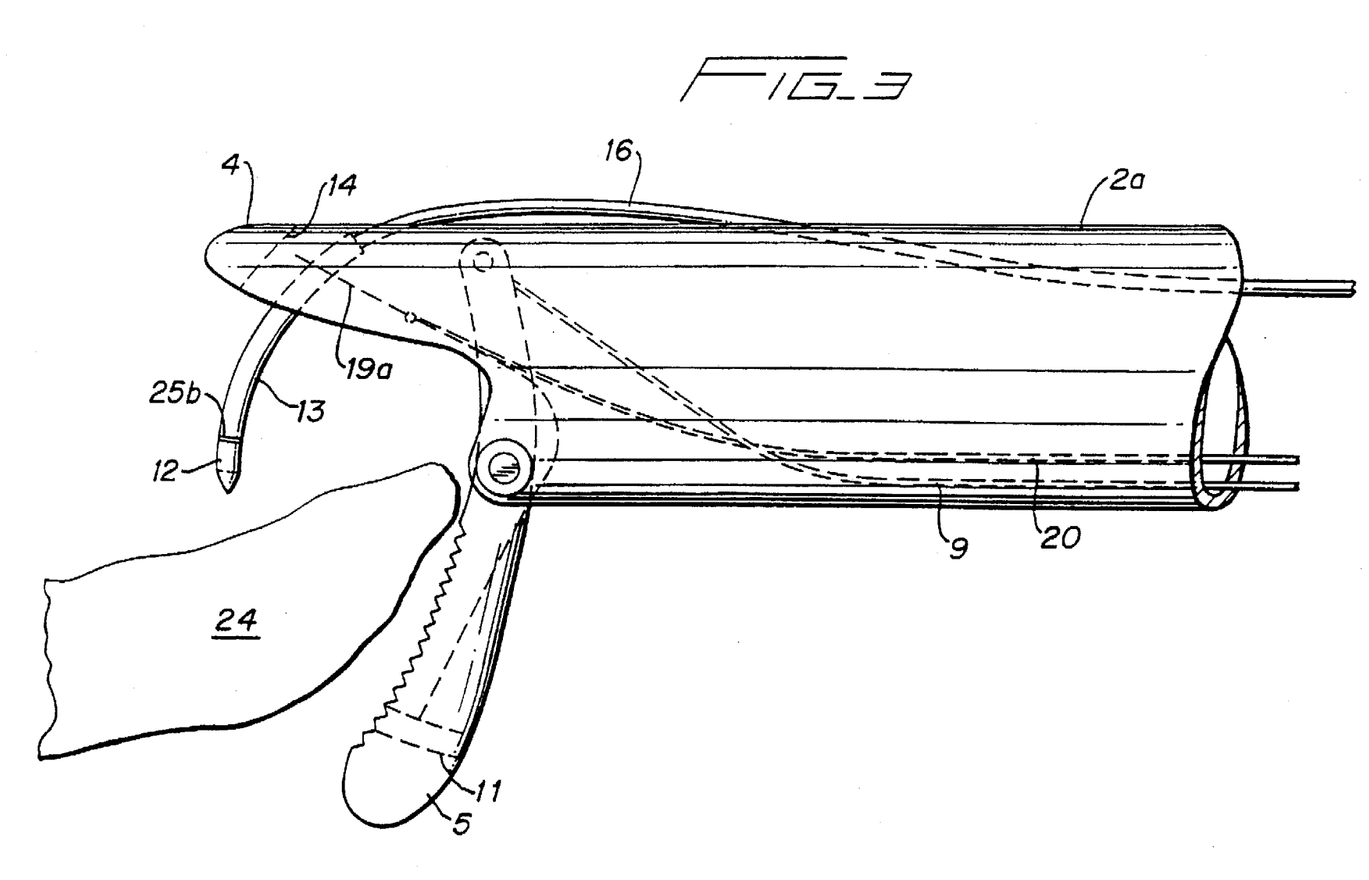
FIGS. 3 to 6 are views of the detailed part of the apparatus shown in FIG. 2 in use.

Next the trigger 10 is manipulated to push control cable 9 forward causing the lower jaw 5 to pivot about pivot mechanism 8 to the open position shown in FIG. 3. It should be noted that the securing arm 19a remains in engagement with the upper portion 15 of the needle 13 and is thereby secured in slot 14. Body tissue to be sewn is then placed between jaws 4 and 5 as shown in FIG. 3 with the needle tip 12 located above the tissue.

Figure 4:
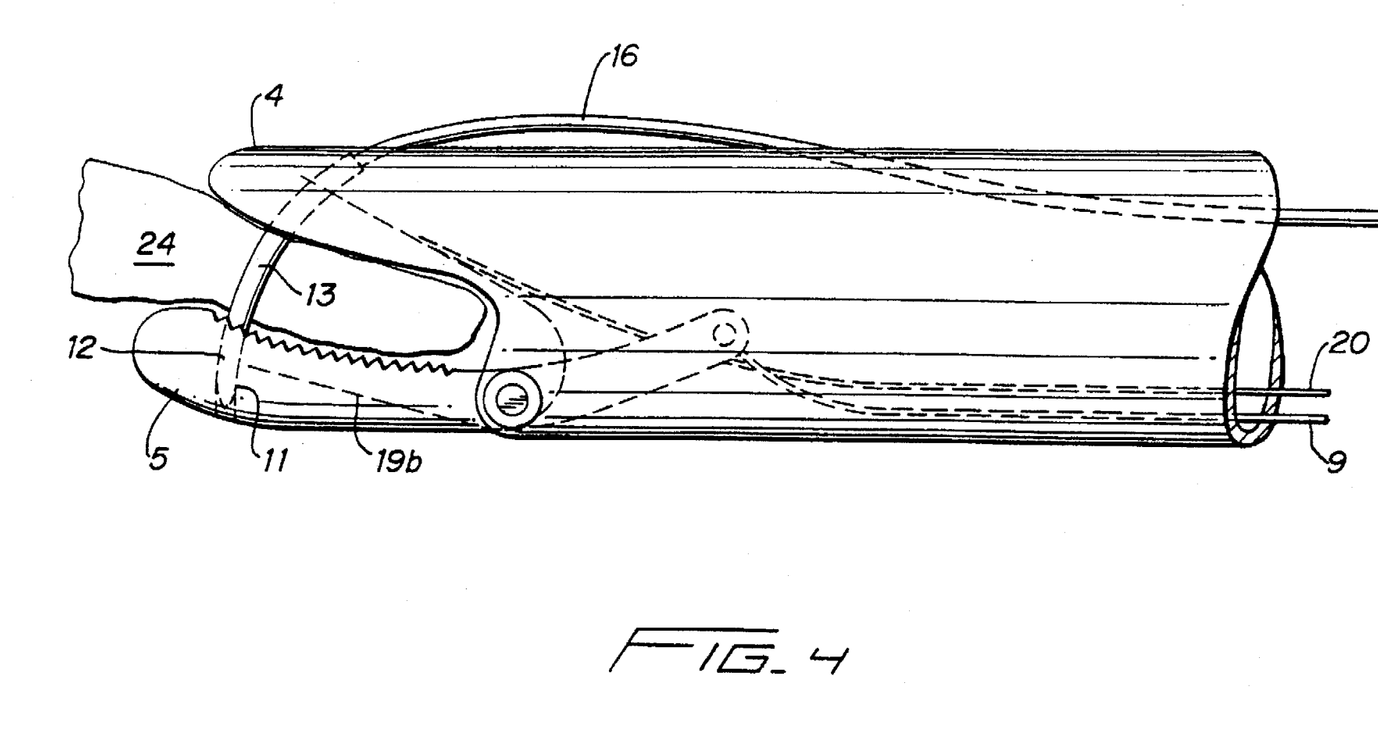

Subsequently, as shown in FIG. 4, the cable 9 is retracted causing jaws 4,5 to pivotally close, in so doing forcing the needle 13 through the tissue 24 such that the needle tip 12 is relocated in the bore 11. Once this stage has been effected, cable 20 is retracted causing the "U" shaped securing member to slide and flex along its length with the lower arm 19b intersecting the bore 11 and engaging with notch 25b in the tip 12 of the needle 13, securing the needle relative to the lower jaw 5. The jaws 4,5 are then opened by forward motion of cable 9 as previously described causing needle 13 to be pulled clean through the tissue 24.

Figure 6:
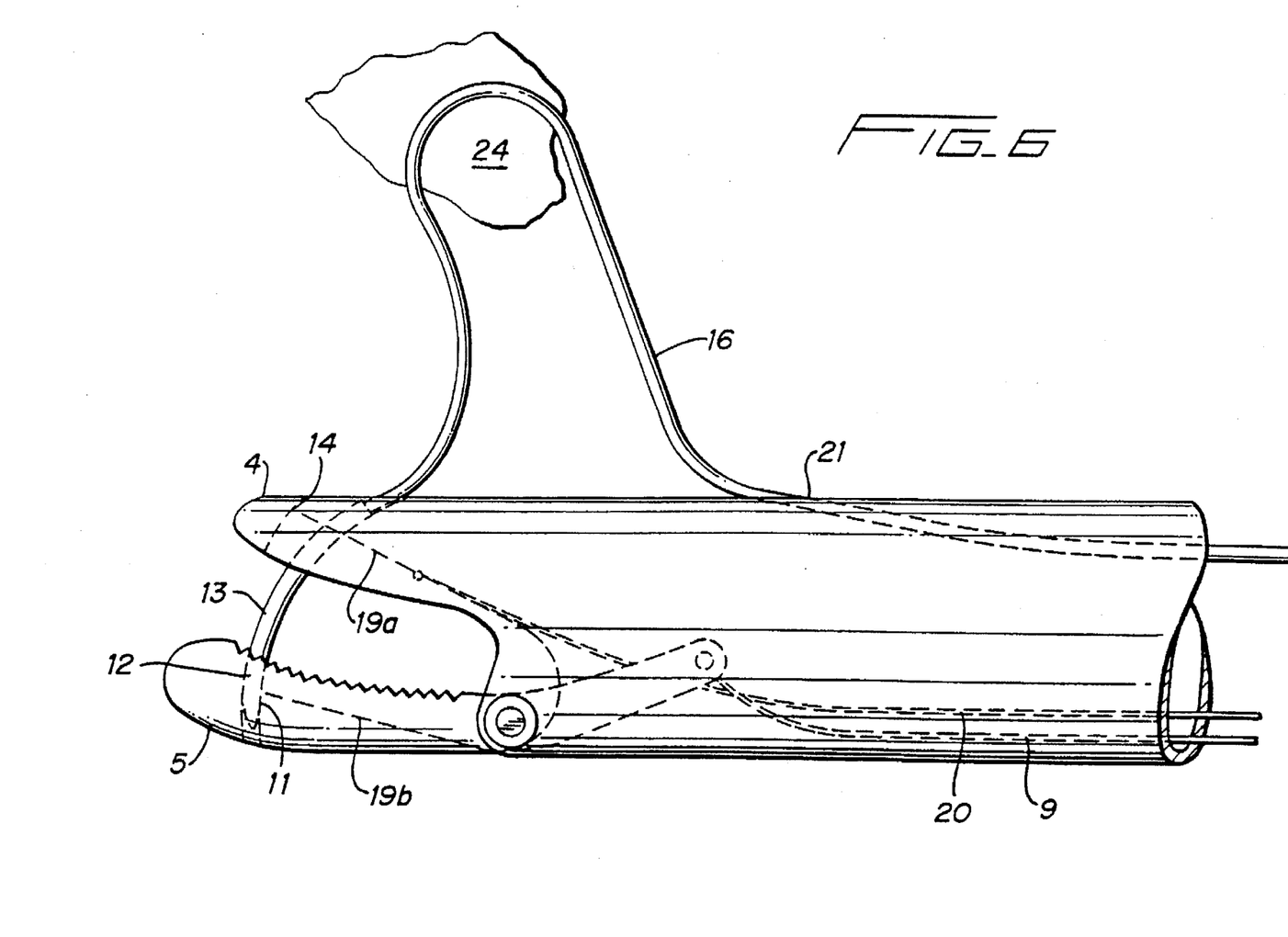

The next step, as shown in FIG. 5, is for the thread 16 to be removed from the slot 14 by moving the arm 2 in the direction of arrow B, causing the thread 16 to move relatively from the apex 17 of the slot 14 towards the mouth 18 in the direction of arrow A in FIG. 7. As can be seen in FIG. 5, once this stage is reached, the needle 13 is secured in the lower jaw 5 with needle 13 and thread 16 passing through the tissue 24. The thread 16 is then pulled further through the tissue 24 and the jaws 4,5 subsequently closed as described previously, causing the upper needle portion 15 to re-engage in slot 14. The upper securing arm 19a is then re-engaged in slot 14 (causing the lower securing arm to be simultaneously retracted from blind bore 11) securing the needle relative to the upper jaw 4 as shown in FIG. 6. by this stage, a complete pass of the suture thread 16 through tissue 24 has been completed, and further passes may be made by repeating the steps outlined above and described in relation to FIGS. 2 to 6. To enable the suture thread local to the needle to re-engage slot 14, a portion of it is relatively stiffened during manufacture, typically by the application of a stiffening agent e.g. epoxy resin. The stiffened portion of the thread whilst being flexible enough to pass through the tissue would direct the thread to return to slot 14 thus enabling the end 15 of the needle 13 to re-engage in slot 14.

The apparatus described enables suturing to be effected easily and efficiently, with the medical operative remote from the needle tip and tissue being sutured.

We claim:

1. A surgical suturing apparatus comprising:

an elongated tubular portion dimensioned for insertion through a trocar cannula, the elongated tubular portion having a proximal end portion and a distal end portion;

first and second jaws extending from the distal end portion of the elongated tubular portion and being relatively movable with respect to one another from an open position to a closed position;

a surgical needle positioned in the first jaw and transferable between the first and second jaws;

a handle mechanism positioned at the proximal end portion of the elongated tubular portion and operatively connected to at least one of the jaws;

a securing mechanism cooperating with the surgical needle and movable between a first position to retain the needle in the first jaw and allow release from the second jaw and a second position to retain the needle in the second jaw and allow release from the first jaw, the securing mechanism being operatively connected to the handle mechanism; and wherein actuation of the handle mechanism closes the jaws and moves the securing member between the first and second positions.

2. A surgical suturing apparatus according to claim 1, wherein the elongated tubular portion is hollow and of substantially uniform outer diameter.

3. A surgical suturing apparatus according to claim 2, wherein the first and second jaws in the closed position together have an outer diameter substantially equal to the outer diameter of the tubular portion.

4. A surgical suturing apparatus according to claim 2, wherein the securing mechanism includes first and second elongated arms extending through the first and second jaws, respectively.

5. A surgical suturing apparatus according to claim 1, wherein the first and second jaws are pivotably connected at a pivot point at a proximal end portion thereof, the pivot point being at the distal end portion of the tubular portion.

6. A surgical suturing apparatus according to claim 5, wherein the securing mechanism includes first and second elongated arms extending through the first and second jaws, respectively.

7. A surgical suturing apparatus according to claim 6, wherein the handle mechanism includes a pivotable trigger member extending transversely of the tubular portion.

8. A surgical suturing apparatus according to claim 7, further comprising a connecting member connecting the first and second elongated arms to the pivotable trigger member.

9. A surgical suturing apparatus according to claim 1, wherein the securing mechanism is connected at a proximal end to the handle portion and extends through the length of the elongated tubular portion through the first and second jaws.

10. A surgical suturing apparatus according to claim 9, wherein actuation of the handle mechanism initially closes the jaws and subsequently moves the securing mechanism.

11. A surgical suturing apparatus according to claim 1, wherein the handle mechanism includes a handle member which pivots with respect to the elongated tubular portion at the proximal end portion thereof, and the first and second jaws are relatively movable with respect to the elongated portion at the distal end portion thereof.

12. A surgical suturing apparatus according to claim 11, further comprising a connecting member extending through the elongated tubular portion operatively connecting a pivotable handle member of the handle mechanism with the first and second jaws.

13. A surgical suturing apparatus according to claim 12, wherein the securing mechanism extends from the handle mechanism through the elongated tubular portion and through the first and second jaws.

14. A surgical suturing apparatus according to claim 13, wherein the jaws are connected at a common point.

15. A surgical suturing apparatus according to claim 1, wherein a recess is formed in each of the jaws and is configured for receiving the needle, each recess being spaced proximally of a distalmost tip of the respective jaw.

16. A surgical suturing apparatus according to claim 1, wherein a recess is formed in each of the jaws, the recesses configured to receive the surgical needle and positioned opposite one another when the jaws are in the closed position.

17. A surgical suturing apparatus comprising:

an elongated tubular body portion;

a handle mechanism positioned at a proximal end portion of the elongated portion;

first and second jaws positioned at a distal end portion of the elongated body portion and relatively movable between an open and closed position, each of the jaws having a needle receiving recess formed therein;

a securing mechanism movable with respect to the first and second jaws to alternately retain and allow release of a surgical needle in the respective needle receiving recess;

wherein actuation of the handle mechanism effects relative movement of the jaws and effects movement of the securing mechanism.

18. A surgical suturing apparatus according to claim 17, wherein the securing mechanism comprises first and second arms extending through the first and second jaws, respectively.

19. A surgical suturing apparatus according to claim 18, wherein the handle mechanism extends transversely of the elongated body portion.

20. A surgical suturing apparatus according to claim 19, wherein each of the recesses are spaced proximally of a distalmost tip of the jaws.

21. A surgical suturing apparatus according to claim 17, wherein the securing mechanism is connected at a proximal end to the handle mechanism and extends through the length of the elongated tubular portion and through the first and second jaws.

22. A surgical suturing apparatus according to claim 21, wherein the jaws are connected at a common pivot point at the distal end portion of the elongated tubular portion.

23. A surgical suturing apparatus according to claim 22, further comprising a connecting member extending through the elongated tubular portion operatively connecting the jaws to the handle portion.

24. A surgical suturing apparatus according to claim 23, wherein actuation of the handle mechanism initially effects relative movement of the jaws and subsequently effects movement of the securing mechanism.

25. A surgical suturing apparatus according to claim 23, wherein the handle mechanism includes a pivotable handle extending transversely of the tubular portion and the connecting member is operatively connected to the pivotable handle.

* * * * *